United States Patent [19]
Salome et al.

[11] Patent Number: 5,482,844
[45] Date of Patent: Jan. 9, 1996

[54] ENZYME INTENDED FOR THE FRAGMENTATION OF N-ACETYLHEPAROSAN, PRODUCTION OF PREPARATIONS CONTAINING THIS ENZYME AND FRAGMENTATION PROCESSES USING THIS ENZYME

[75] Inventors: Marc Louis V. Salome; Philippe Lelong, both of Castanet Tolosan, France

[73] Assignee: Elf Sanofi, Paris, France

[21] Appl. No.: 20,396

[22] Filed: Feb. 22, 1993

[30] Foreign Application Priority Data

Feb. 26, 1992 [FR] France ................................ 92 02255

[51] Int. Cl.[6] ........................... C12P 19/26; C12P 19/14; C12P 19/04
[52] U.S. Cl. ....................... 435/84; 435/99; 435/101; 514/56; 536/21

[58] Field of Search ................... 435/71.1, 99, 101, 435/84; 536/21; 514/56

[56] References Cited

U.S. PATENT DOCUMENTS

| 4,401,758 | 8/1983 | Lormeau et al. | 514/56 |
| 4,704,360 | 11/1987 | Shoham et al. | 435/99 |
| 4,818,817 | 4/1989 | Shoham | 435/101 |
| 5,106,734 | 4/1992 | Nielsen | 435/84 |

OTHER PUBLICATIONS

BioTech Abs 92–10267 EP–489647 (Jun. 10, 1992).

*Primary Examiner*—Herbert J. Lilling
*Attorney, Agent, or Firm*—Jacobson, Price, Holman & Stern

[57] ABSTRACT

The invention relates to an enzyme capable of fragmenting a high molecular mass N-acetylheparosan. This enzyme was obtained with the strain *Escherichia coli* (K5), strain SEBR 3282.

12 Claims, 7 Drawing Sheets

ENZYME INTENDED FOR THE FRAGMENTATION OF N-ACETYLHEPAROSAN, PRODUCTION OF PREPARATIONS CONTAINING THIS ENZYME AND FRAGMENTATION PROCESSES USING THIS ENZYME

The present invention relates to an enzyme intended for the fragmentation of N-acetylheparosan, to the production of preparations containing this enzyme and also to fragmentation processes using this enzyme.

Some bacteria of the species *Escherichia coli* are known to produce a capsular polysaccharide, usually referred to as K5, which is a family of polymers consisting of repeated β-D-glucuronyl- (1→4)-N-acetyl-α-D-gluco-saminyl-(1→4) units (W. F. Vann et al, Eur. J. Biochem, 1981, 116, 359–364), of structure (a):

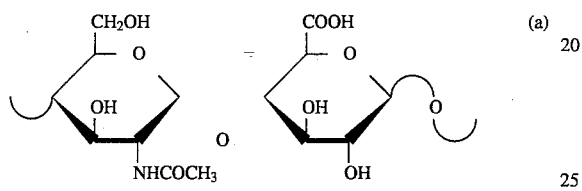

This polysaccharide will be referred to here as "N-acetylheparosan". This product possesses a molecular mass of between $10^5$ and $2 \times 10^6$ Da and, in respect of the "uronic acid" units, a very regular structure composed solely of D-glucuronic acid (W. F. Vann et al, Eur. J. Biochem, 1981, 116, 359–364, and Patent Application EP-A-0,333,243).

N-Acetylheparosan is, most particularly, useful as a starting material for the pharmaceutical industry but, for this use, it has too high a molecular mass.

It is known that N-acetylheparosan (polysaccharide K5) may be fragmented by a phage lyase originating from a phage specific for the strain *Escherichia coli* (K5), but this fragmentation is very extensive and leads to a substantial disappearance of the fragments of molecular mass 5000 Da in favour of much smaller chains (D. Gupta et al, FEMS Microbiology Letters, 1983, 16, 13–17). This fragmentation is used in Patent Application EP-A-0,333,243 for the preparation of fragments containing at most 10 saccharide units.

It is also known that oligosaccharides possessing at the non-reducing end a glucuronic unit having a double bond between carbons 4 and 5 may be obtained by enzymatic depolymerisation of polysaccharides, using as an enzyme the enzyme obtained from *Bacillus circulans*, and in particular from *Bacillus circulans* strain NCIB 12482. This enzyme acts on the glucose-glucuronic acid bonds (EP-0, 294,879). An enzyme obtained from a culture of *Bacillus polymyxa* is also described in U.S. Pat. No. 3,812,012.

Surprisingly, it was found that cultures of *Escherichia coli* (K5), strain SEBR 3282, produce under certain environmental conditions an enzyme which fragments N-acetylheparosan during culture in a fermenter. No less surprisingly, it was also found that the N-acetylheparosan fragments lie around a peak of molecular mass of approximately 5000 Da, representing, apart from a few disaccharide units, an aggregate of approximately 70% of the product.

Lastly, again surprisingly, it was found that a suitably solubilised preparation of this enzyme made it possible to obtain fragments of higher molecular mass than the fragments obtained spontaneously, that is to say with the non-solubilised enzyme. In effect, solubilised enzyme preparations enable the fragmentation to be varied, and fragments to be obtained, the majority of which have a molecular mass at least 1000 to 3000 Da higher than the molecular mass of the fragments obtained spontaneously.

Thus, the subject of the present invention is an enzyme which makes it possible to vary the fragmentation of a high molecular mass N-acetylheparosan, and to obtain N-acetylheparosan fragments of desired molecular mass in very good yield. The enzyme of the present invention is hence useful for preparing low molecular mass N-acetylheparosans from a high molecular mass N-acetylheparosan, for the following reasons:

high molecular mass N-acetylheparosan is obtained on inexpensive synthetic medium in yields higher than those using a complex medium, such a medium being necessary for obtaining a low molecular mass N-acetylheparosan;

high molecular mass N-acetylheparosan is technically easier to handle than that of low molecular mass;

in vitro fragmentation separates the production phase from that of fragmentation, enabling the two phases to be controlled and optimised while affording great latitude with regard to the characteristics of the product sought, for example with regard to its molecular mass;

the enzyme and N-acetylheparosan are especially stable, and this allows multiple recyclings which may be necessary when carrying out dynamic processes, during which the processes of fragmentation and fractionation are carried out simultaneously or successively, while procuring freedom from the time constraints linked to the use of a bioreactor.

More specifically, the enzyme of the present invention is characterised in that:

it is obtained from an *Escherichia coli* (K5) strain, *Escherichia coli* strain SEBR 3282, or from a spontaneous or induced mutant of this strain, its molecular mass is between 62,000 and 70,000 Da, and more specifically between 65,000 Da and 66,000 Da (±1500 DA), its isoelectric point lies in the pH range between 4.7 and 5.4 pH units, and is more specifically 5.1 pH units, it is an eliminase, and more specifically an endo-β-eliminase.

The enzyme of the present invention is also characterised in that it acts in the following manner:

it is of membrane origin, its temperature of optimal functioning (maximum activity) is in the region of 37° C., and the temperature at which it is inactivated is approximately 60° C., the optimal pH range for its functioning lies between the values pH 6 and pH 7, and more specifically between pH 6.6 and pH 6.8, for its functioning, the optimal range of concentration of monovalent or divalent ions lies in the vicinity of 0.2M, and more specifically 0.15M for divalent ions and 0.25M for monovalent ions.

Furthermore, the enzyme of the invention is characterised in that:

it does not permit fission of N-acetylheparosan below a certain size, which size corresponds to a molecular mass of approximately 1000 to 1500 Da, it is capable of acting on high molecular mass N-acetylheparosan and of fragmenting it in the absence of bacterial particles in vitro.

The enzyme which is the subject of the present invention is an enzyme obtained from a culture of *Escherichia coli*, in particular *Escherichia coli* SEBR 3282. This strain is a strain derived from the strain Bi 8337-41 (O10:K5:H4) ATCC 23506 (described by D. S. Gupta et al FEMS Microbiology Letters, 1982, 14, 75–78 and W. Vann Eur. J. Biochem. 1981, 116, 359–364).

The *Escherichia coli* (K5) strain SEBR 3282 responds positively to the typing test with the specific phage K5 according to the method of B. Kaiser et al (J. Clin. Microbiol., (1984), 19, 2, 264–266). Hence it is indeed an *Escherichia coli* (K5) strain. This strain was deposited with the CNCM of the Pasteur Institute, Paris, France, under No. I-1013. It is also possible to isolate this enzyme from a mutant, either spontaneous or induced, of *Escherichia coli* strain SEBR 3282, or alternatively with other suitable *Escherichia coli* (K5) strains, and in particular with the strain Bi 8337-41 (O10:K5:H4) ATCC 23506. It is also possible to envisage obtaining this enzyme with the strain Bi 626-42 (O12: K5:NM) ATCC 23508.

The molecular mass of this enzyme, assessed by exclusion chromatography, is between 62,000 and 70,000 Da, and it is, more specifically, approximately 65,000 Da to 66,000 Da (±1500 Da).

The isoelectric point of the enzyme which is the subject of the present invention lies at a pH of 4.7–5.4, and is more specifically 5.1 pH units.

The enzyme of the invention enables N-acetylheparosan to be fragmented, and fragments to be obtained containing at the non-reducing end a glucuronic acid residue having a double bond between carbons 4 and 5 (elimination of the OH group). Such enzymes do not involve water in the chemical reaction in question, and are termed eliminase type. The enzyme which is the subject of the present invention is hence an eliminase, and in particular an endo-β-eliminase.

The prefix "endo" is used to indicate that the enzyme which is the subject of the present invention is capable of fragmenting N-acetylheparosan at a considerable distance from the end of the molecule. More especially, the enzyme of the present invention does not permit fission of N-acetylheparosan below a certain size, which corresponds to a molecular mass of approximately 1000 Da to 1500 Da. Thus, the enzyme which is the subject of the present invention, during a total fragmentation of a high molecular mass N-acetylheparosan, makes it possible to obtain N-acetylheparosan fragments of molecular masses between 1000 Da and 10,000 Da, and more especially to obtain fragments having molecular masses grouped together comprising 70% in the region of 5000 Da.

This high molecular mass N-acetylheparosan which can be fragmented by the enzyme which is the subject of the present invention may be obtained as described by W. F. Vann et al, Eur. J. Biochem, 1981, 116, 359–364, and in Patent Application EP-A-0,333,243, or alternatively by fermentation of the same strain *Escherichia coli* (K5) SEBR 3282 used for the preparation of the enzyme of the present invention.

By the action of the enzyme of the present invention, high molecular mass N-acetylheparosan is fragmented into fragments having a predominant molecular mass of approximately 5000 Da. The term "predominant molecular mass" is understood to mean the molecular mass which corresponds to the maximum (peak) of the chromatographic profile obtained on determination of the molecular mass of the N-acetylheparosan by gel permeation chromatography (GPC). The fragments thereby obtained possess at the non-reducing end a glucuronic unit having a double bond between carbons 4 and 5.

This enzyme makes it possible, in particular, to obtain at the end of culturing, from a high molecular mass N-acetylheparosan, a majority of fragments having identical sizes which correspond to a molecular mass of approximately 5000 Da. Hence the enzyme of the invention must be capable of interacting with the N-acetylheparosan macromolecule at a given distance from the end of this macromolecule. It is hence an endo-eliminase which enables a majority of fragments consisting of an identical number of β-D-glucuronyl-(1→4)-N-acetyl-α-D-gluco-saminyl-(1→4) units to be obtained.

Monitoring of the spontaneous fragmentation of N-acetylheparosan during culture in a complex medium also brings to light a phenomenon of mild lysis which makes it difficult to foresee where the enzyme in question is localised in the cell: cytoplasm, periplasm, membrane or alternatively extracelluar culture medium.

The methods employed to localise the endo-β-eliminase are defined and collated in Scheme 1 as described in FIG. 6.

Figure 6:
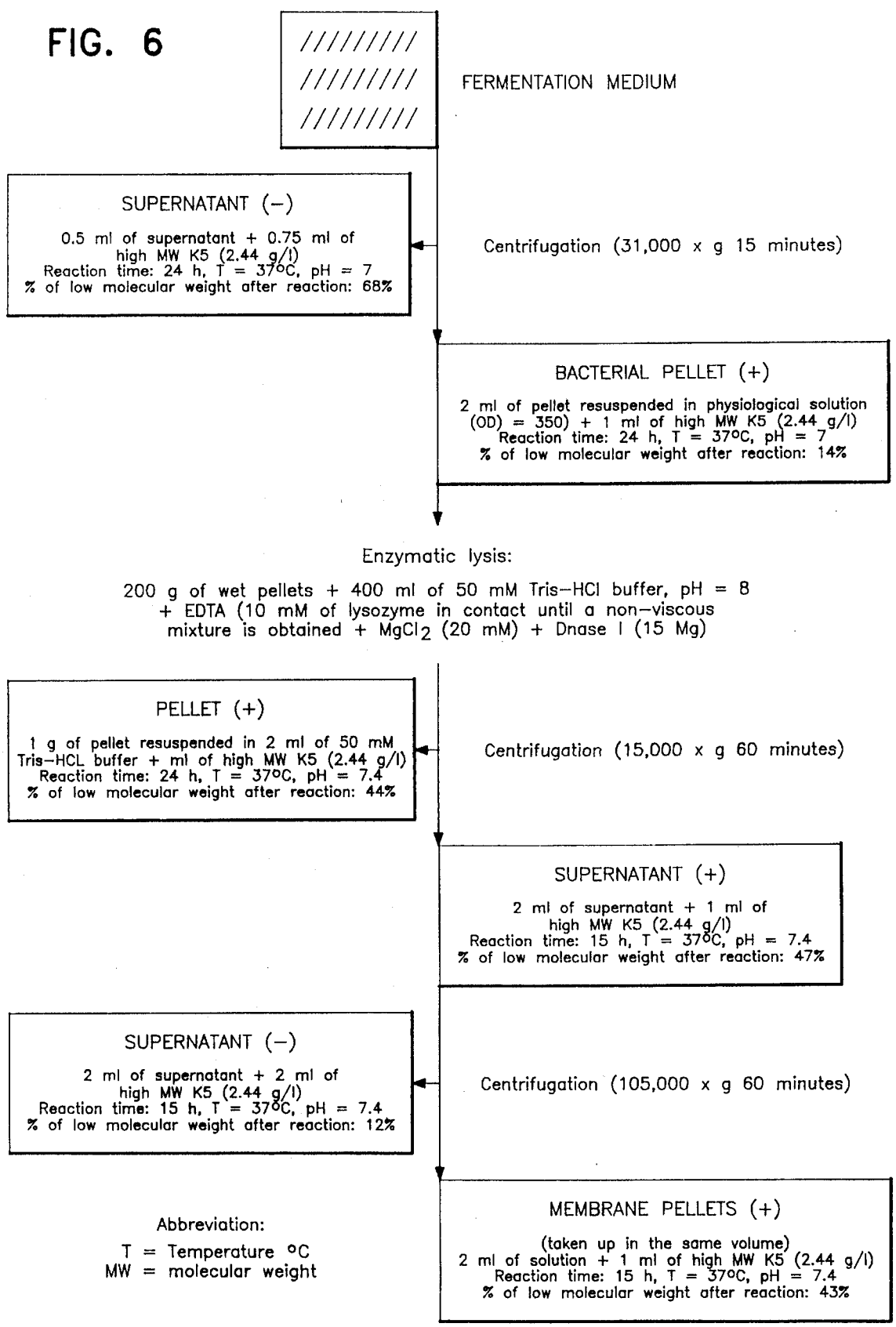
FIG. 6 shows Scheme 1 which collates the methods used to localize the endo-β-eliminase.

It is observed in FIG. 6 that:
the supernatant of the suspensions of culture of *Escherichia coli* (K5) strain SEBR 3282 on "complex medium" contains small amounts of endo-β-eliminase;
the major part of the enzymatic activity lies in the crude bacterial pellets;
the lipid membrane preparations obtained from the lysis supernatants of the washed pellets contain the major part of the β-eliminase type activity.

Consequently:
the enzyme is originally membrane-bound and, without further manipulation, the major part of the activity occurs in the lipid membranes of the bacteria;
during culture in liquid medium, and especially with stirring, as well as under conditions of lysis of the bacterial particles, a part of the activity may occur and be exerted outside the bacterial particles;
it is not necessary to concentrate the enzyme; to obtain it, it suffices to isolate lipid membranes.

The enzyme which is the subject of the present invention is hence an enzyme of membrane origin, the major part of the activity occurring in lipid membranes of the bacteria. However, during culture in liquid medium, and especially with stirring, as well as under conditions of lysis of the bacterial particles, a part of the activity may occur and be exerted outside the bacterial particles.

The solubilisation of the enzyme of the present invention was established using different detergents according to known techniques (Biotechnology and Applied Biochemistry, 1990, 12, 599–620), starting with a membrane pellet.

Thus, for example, enzyme preparations solubilised with detergents such as Triton X-100®, Triton X-114®, DOC, NP-40®, Tween 80®, all at a concentration of 2%, and 0.1M guanidine hydrochloride are active. The enzyme may also be obtained in solubilised form by subjecting the crude bacterial pellet to an alkaline lysis.

The determination of the isoelectric point (pHi) of the enzyme was performed according to the "chromatofocusing" method, in a pH range between 3.5 and 9. The phi of the enzyme thus determined lies between pH 4.7 and PH 5.4, more specifically at 5.1 pH units.

The molecular mass of the enzyme of the present invention was determined by gel permeation chromatography (GPC), and lies between 62,000 and 70,000, the protein peak being at approximately 65,000–66,000 Pa (±1500 Da).

The enzyme of the present invention, in the form of a membrane preparation, was also subjected to tests to study the environmental factors that exert an influence on its activity. Thus, the influence of temperature, pH, monovalent ions, in particular the $Na^+$ ion, and divalent ions, in particular the $Ca^{2+}$ is known. The Michaelis constant was also determined, and the stability of the enzyme under certain conditions was observed.

The optimal temperature of functioning of the enzyme (maximal activity) which is the subject of the present invention is in the region of 37° C. The inactivation temperature of the enzyme is 60° C. and at a temperature of 20° C. the enzyme retains 40% of its activity in comparison to that at 37° C.

The optimal pH range of functioning of the enzyme which is the subject of the present invention lies between the values pH 6 and pH 7, and is more specifically pH 6.6 to pH 6.8.

Moreover, the optimal range of concentration of monovalent ions, and more especially sodium ions, for the functioning of the enzyme which is the subject of the present invention lies in the vicinity of 0.2M, and more specifically at approximately 0.25M.

For divalent ions, the optimal concentration range for the functioning of the enzyme also lies in the vicinity of 0.2M, and more specifically at approximately 0.15M. In effect, when the enzyme is used dissolved in 0.2M calcium chloride, an approximately 100% activation is observed relative to the control without $Ca^{2+}$ ion.

The invention also relates to a process for production of the enzyme which is the subject of the present invention, and in particular the production of preparations containing this enzyme from a culture of *Escherichia coli* (K5) strain SEBR 3282, or from a mutant, either spontaneous or induced, of the strain SEBR 3282. However, it is also possible to obtain this enzyme with other suitable *Escherichia coli* (K5) strains, for example with the strain Bi 8337-41 (010:K5:H4) ATCC 23506. It is also possible to envisage obtaining this enzyme with *Escherichia coli* (K5) strain Bi 626-42 (012:K5:NM) ATCC 23508.

More especially, the invention also relates to a process for production of the enzyme which is the subject of the present invention, in the form of crude bacterial pellets containing it, characterised in that culturing of *Escherichia coli* (K5) SEBR 3282 or of a spontaneous or induced mutant of this strain, or of another suitable *Escherichia coli* (K5) strain, is performed in a culture medium favourable to the formation of this enzyme, and in that the pellet is isolated from the culture by centrifugation, for example at 10,000×g.

The invention also relates to a preparation containing the enzyme which is the subject of the present invention, consisting of a crude bacterial pellet obtained from a culture of *Escherichia Coli* (K5) SEBR 3282 or of a spontaneous or induced mutant of this strain, containing this enzyme.

The invention also relates to a process for production of the enzyme which is the subject of the present invention, in the form of crude lysates containing it, characterised in that culturing of *Escherichia coli* (K5) SEBR 3282 or of a spontaneous or induced mutant of this strain is performed in a culture medium favourable to the formation of this enzyme, the pellet is isolated from the culture and this pellet is subjected to a lysis.

The preparations containing the enzyme which is the subject of the present invention, consisting of a crude lysate obtained by lysis of a crude bacterial pellet containing this enzyme, also form part of the present invention.

The invention also relates to a preparation containing the enzyme which is the subject of the present invention, consisting of a membrane preparation obtained by lysis of a bacterial pellet containing this enzyme, and then by separation of the membranes from the lysate of the bacterial pellet.

The invention also relates to the preparations containing the enzyme in solubilised form.

These preparations may be obtained by solubilising the enzyme contained in a membrane preparation using anionic or cationic detergents.

They may also be obtained by subjecting a crude bacterial pellet containing this enzyme to a partial lysis in an alkaline medium.

The term "preparation containing the enzyme" clearly includes the preparations of the enzyme in the form of crude bacterial pellets, as well as the crude lysates obtained from a culture of *Escherichia coli* (K5) strain SEBR 3282, or with a mutant, either spontaneous or induced, of the strain.

The term "preparation containing the enzyme" also includes the membrane preparations obtained from a crude lysate containing the enzyme which is the subject of the present invention.

The term "preparation containing the enzyme" also includes the solubilised enzyme preparations obtained with membrane preparations containing the enzyme which is the subject of the present invention, as well as the solubilised enzyme preparations obtained after alkaline lysis of the crude bacterial pellets containing the enzyme which is the subject of the present invention.

The term "preparation containing the enzyme" also includes any other preparation containing the enzyme, alone or in combination with another enzyme or organic or inorganic substances.

To obtain a crude bacterial pellet containing the enzyme which is the subject of the present invention, the pellet of the suspension of an *Escherichia coli* (K5) strain SEBR 3282 culture performed under environmental conditions favourable to the formation of the enzyme which is the subject of the present invention is used. This pellet is isolated from the suspension of an *Escherichia coli* (K5) strain SEBR 3282 culture by standard methods, for example by centrifugation.

In effect, an eliminase type activity is observed, during culturing of *Escherichia coli* (K5) strain SEBR 3282, only under certain conditions:

1- the culture medium must contain an inducer of the synthesis of the enzyme, which can be either complex like yeast extract, or pure like N-acetylglucosamine;

2- the culture medium must, in addition, contain an amino acid mixture such as, for example, casein hydrolysate (HY-CASE SF -Sheffield® USA), or alternatively a mixture of synthetic amino acids made from pure amino acids as described in the formulation of medium E;

3- the carbon source used can be glucose or glycerol. The latter compound does not, however, enable significant eliminase activity to be obtained.

To observe maximal eliminase activity, several factors must hence participate synergistically:

actual inducing factors;

synthesis-regulating factors such as the nitrogen and carbon sources;

environmental factors that influence the activity of the enzyme itself or of its interaction with the substrate, such as monovalent or divalent ions, temperature, pH or the like.

Moreover, the kinetics of eliminase activity during culture shows that either the synthesis of the enzyme takes place mainly during the post-exponential phase of culture, or the persisting enzyme is activated during this phase of culture.

It is hence apparent that induction of the enzyme may be sought in a rational manner using synthetic media which simultaneously fulfil the conditions described above.

Medium E, the composition of which is given in Table I below, enables the formulation of efficacious culture media free from complex starting materials of animal origin to be envisaged.

TABLE I

Composition and preparation of medium E
MEDIUM E

Medium E is obtained by combining the following two sterile solutions 1 and 2:
Solution No. 1

In 700 ml of ultrapurified water, dissolve in order:
| | |
|---|---|
| Complexing agent: N-[Tris(hydroxymethyl)-methyl]glycine (Tricine marketed by Fluka ®) | 360 mg |
| $K_2HPO_4$ | 790 mg |
| $M_gCl_2 \cdot 6H_2O$ | 620 mg |
| $K_2SO_4$ | 610 mg |
| $FeSO_4 \cdot 7H_2O$ | 25 mg |
| $CaCl_2 \cdot 2H_2O$ | 2 mg |
| NaCl | 500 mg |
| KCl | 5000 mg |
| KI | 10 mg |
| Yeast extract | 18000 mg |

Heat gently, adjust the pH to 7.4, then make the volume to 750 ml with ultrapurified water and autoclave for 30 minutes at 120° C.
Solution No. 2

Dissolve in 100 ml:
| | |
|---|---|
| Glutamic acid | 17.8 g |
| Proline | 1.6 g |
| Methionine | 0.4 g |
| Glycine | 0.75 g |
| Arginine | 1.25 g |
| Cysteine | 0.20 g |
| $K_2HPO_4$ | 1.56 g |
| Solution of trace elements (see TABLE II below) | 1 ml |
| Glucose | 18 g |

Adjust the pH to 7.4 with KOH. Make the volume to 167 ml with ultrapurified water and perform a sterilising filtration through a 0.2 μm membrane

TABLE II

Preparation of the solution of trace elements in 800 ml of ultrapurified water, dissolve (in order):
| | |
|---|---|
| $H_3BO_3$ | 500 mg |
| $Na_2MoO_4 \cdot 2H_2O$ | 1930 mg |
| $CoCl_2 \cdot 6H_2O$ | 11850 mg |
| $CuSO_4 \cdot 5H_2O$ | 25 mg |
| $ZnSO_4 \cdot 7H_2O$ | 2000 mg |
| $AlCl_3 \cdot 6H_2O$ | 2410 mg |

As a culture medium, there may also be mentioned, as a non-exclusive example, a complex medium as described in the present invention, and in particular "medium D" for preculture of *Escherichia coli* (K5) strain SEBR 3282, and "medium C" for culture of this preculture.

To obtain a crude lysate containing the enzyme which is the subject of the present invention, the pellet of the suspension of an *Escherichia coli* (K5) strain SEBR 3282 culture set up under environmental conditions favourable to the formation of the enzyme which is the subject of the present invention is used, and more especially the crude bacterial pellets containing the enzyme. In effect, at the end of this culturing, the pellet of the suspension of the strain SEBR 3282 culture is recovered by centrifugation and then lysed, for example by addition of lysozyme. This crude lysate thereby obtained may be used directly.

The membrane preparations containing the enzyme which is the subject of the present invention are obtained from the crude lysate by successive centrifugation enabling the membrane pellets to be isolated, which pellets are then solubilised, either in ultrapurified water or in suitable buffers such as, for example, Tris-HCl buffer, pH 7.2. it is also possible to use aqueous solutions containing monovalent or divalent ions, in particular $Na^+$ or $Ca^{2+}$ ions.

The solubilised enzyme preparations are obtained from membrane preparations containing this enzyme. In effect, the enzyme which is the subject of the present invention may be solubilised from membrane preparations and obtained in active form.

In order to solubilise it, detergents, salts, enzymes or any other means known to a person skilled in the art may be used. In effect, the enzyme which is the subject of the present invention may be solubilised from lipid preparations using certain detergents without being denatured.

As detergents, nonionic detergents may be used more especially. As examples, Triton X-100®, Triton X-114®, deoxycholate (DOC), NP-40®, Tween 80® and 0.1M guanidine HCl may be mentioned. However, demonstration of the enzymatic activity of the enzyme which is the subject of the present invention necessitates removal of the detergent residues using, for example, specific, commercially available affinity columns.

The enzyme which forms the subject of the present invention may also be solubilised in an undenatured manner without making use of detergents, by partial lysis in an alkaline medium. As an alkaline medium (pH approximately 11), solutions of strong inorganic bases such as sodium hydroxide or potassium hydroxide may be used. Potassium hydroxide is preferred.

The invention also relates to processes for fragmentation of high molecular mass N-acetylheparosans employing preparations of the enzyme which is the subject of the present invention.

These processes can employ the enzyme which is the subject of the present invention either in culture media in vivo during the production of N-acetylheparosans, or in vitro in the case where the phase of production of N-acetyl-heparosan is separated from that of fragmentation. In the latter case, the preparations of the enzyme which is the subject of the present invention are used only in the fragmentation phase.

The enzymatic reaction is performed at between pH 4.0 and pH 9.0, and preferably between pH 6.4 and pH 7.4.

The in vivo demonstration of the enzyme was accomplished by the induced fragmentation of a quantity of high molecular mass N-acetylheparosan added to a culture suspension possessing eliminase activity.

It was confirmed that the enzyme thereby obtained cuts high molecular mass N-acetylheparosan so as to obtain an N-acetylheparosan composed predominantly of fragments of molecular mass 5000 Da. Hence the phenomenon does not represent a halting of the synthesis of high molecular mass N-acetylheparosan by the bacterium, but a subsequent modification of the polymer.

It was found, surprisingly, that the molecular mass of the N-acetylheparosan obtained by fragmentation performed with the enzyme of the present invention may be varied by using a solibilised enzyme preparation or alternatively by carrying out the enzymatic reaction in the presence of cations, in particular $Na^+$ ions.

Thus, according to a further aspect, the present invention relates to a process for the preparation of N-acetylheparosan having molecular masses grouped together, lying, in particular, between 2000 and 10,000 Da, characterised in that high molecular mass N-acetylheparosan (polysaccharide K5) is treated with the enzyme of the present invention in the presence of a solution of sodium chloride having, in particular, a molarity of 0.2 to 0.5M.

The term "molecular masses grouped together between 2000 and 10,000 Da", as used here, relates to the different N-acetylheparosans having a molecular mass with a fairly narrow distribution curve, for example 1000 to 3000 Da with predominant molecular mass at 2000 Da, from 3200 to 4000 Da with predominant molecular mass at 3600 Da, from 3900 to 4700 Da with predominant molecular mass at 4300 Da, from 6000 to 8000 Da with predominant molecular mass at 7000 Da, and from 8000 to 10,000 Da with predominant molecular mass at 9200 Da. It is understood that these molecular masses refer to the majority of the constituents, namely between approximately 50% and approximately 90%. The molecular mass of the products thereby obtained depends, in particular, on the molarity of the medium with respect to sodium chloride in the reaction medium, as well as on the form, solubilised or otherwise, of the enzyme.

The process of the present invention may also be performed by binding the high molecular mass N-acetylheparosan to a column of ion exchange resin and treating the product bound to the column with a solution of the enzyme of the present invention.

On eluting with a solution containing 0.2 to 0.5M sodium chloride, N-acetylheparosan having the desired molecular mass, depending on the molarity with respect to sodium chloride of the solution used, is obtained. For this variant, anion exchange resins, for example a Q Sepharose® type resin or other equivalent resins, may be used as the resin.

Moreover, in view of the fact that the enzyme which is the subject of the present invention is active over a wide range of sodium chloride concentrations, it is possible to envisage the use of the enzyme in processes which permit a fragmentation and a simultaneous fractionation of the N-acetylheparosan bound to the column.

The invention also relates to processes for preparation of low molecular mass N-acetylheparosans using the enzyme which is the subject of the present invention in immobilised form.

The invention also relates to the use of the enzyme for the fragmentation of high molecular mass N-acetylheparosans.

For the preparation of low molecular mass N-acetylheparosans, it is also possible to envisage a process that combines a step of fragmentation of a high molecular mass N-acetylheparosan with the enzyme which is the subject of the present invention, and an alcohol fractionation step or an ultrafiltration step.

The examples which follow illustrate the invention without, however, limiting it. In the PREPARATION and in the EXAMPLES, trade names whose meanings are clarified below have been used:

Triton X-100®: polyethylene glycol tert-octylphenyl ether (Rohm & Hass Co.)

Triton X-114®: polyethylene glycol tert-octylphenyl ether (Rohm & Hass Co.)

DOC: deoxycholic acid sodium salt

NP-40®: Nonidet® P-40, ethylphenylpolyethylene glycol (Shell)

Tris-HCl: Tris(hydroxymethyl)aminomethane hydrochloride

Tween 80®: polyoxyethylene sorbitan monooleate (Atlas Chem. Ind. Inc)

Struktol J 673®: antifoam of Schill & Seilacher - Germany/Hamburg Germany/Hamburg

PREPARATION

N-Acetylheparosan Predominantly of High Molecular Mass 400 ml of medium B of composition specified in Table III below, are inoculated with *Escherichia coli* (K5) strain SEBR 3282 deposited with the CNCM of the Pasteur Institute, Paris - France, under No. I-1013, and the suspension is incubated with stirring for 2 h at 37° C. The preculture obtained is then transferred to an 8.5-1 fermenter containing 11 ml of medium A, of composition also specified in Table III below, and the suspension is incubated for 6 h 30 minutes at 37° C. and pH 7.2, the oxygen partial pressure being maintained at 40 mmHg by regulating the injection of air (up to 20 l minute) and with stirring. Glycerol is then added by introducing in continuous fashion a sterile solution containing 500 g/l of glycerol at the rate of 18 g/h for 16 to 17 hours.

Culturing is continued under the same temperature, pH and oxygen partial pressure conditions until virtually all the glycerol has been consumed. Monitoring of the optical density (OD) at λ=600 nm of the culture suspension after the addition of glycerol has been completed shows a stationarystate or state of mild lysis until culturing is halted at 28–30 h of age in the fermenter.

TABLE III

Composition and preparation of medium A and medium B

| MEDIUM A | |
|---|---|
| In 900 ml of ultrapurified water, dissolve in order: | |
| NTA (nitrilotriacetic acid)* | 1000 mg |
| $K_2HPO_4$ | 790 mg |
| Glutamic acid | 11000 mg |
| $MgCl_2.6H_2O$ | 500 mg |
| $K_2SO_4$ | 450 mg |
| $FeSO_4.7H_2O$ | 18 mg |
| $CaCl_2.2H_2O$ | 2 mg |
| NaCl | 500 mg |
| KCl | 5000 mg |
| Solution of trace elements (see Table II) | 1 ml |
| Glycerol | 10000 mg |

Adjust the pH to 7.2 with concentrated potassium hydroxide of density 1.38, and make to 1000 ml with ultra-purified water. Perform a sterilising filtration through a 0.2 µm membrane.

Glycerol solution

Dissolve 50 g of glycerol in an appropriate quantity of ultra-purified water and adjust the volume to 1000 ml with the same solvent. Perform a sterilising filtration through a 0.2 µm membrane. The antifoam employed during fermentation is Struktol J 673 ® (Schill and Seilacher).

TABLE III-continued

Composition and preparation of medium A and medium B

MEDIUM A

MEDIUM B

The preparation of medium B is identical to that of medium A except that, in addition, the buffer (pH 7.2) 3-morpholinopropanesulphonic acid (MOPS) should be added after addition of the antifoaming agent.

* The quantity of NTA used for the preparation of medium B may be replaced by an appropriate quantity of N-[tris-(hydroxymethyl)methyl]glycine (Tricine marketed by Fluka ®), which is 360 mg.

The culture broth is then cooled to 25° C. 5 liters of culture are withdrawn and centrifuged (11,000–14000×g) for 15 to 20 min. The supernatant is mixed with 5 liters of culture. The centrifugation operation is repeated. The pellet is removed and the supernatant is filtered through a 0.2 μm polycarbonate screen membrane (Nucleopore®). The filtrate obtained is concentrated using an Amicon® hollow-fibre cartridge, cut-off threshold 30,000 Da, or equivalent. A solution enriched in high molecular mass N-acetylheparosan is thereby obtained. An appropriate quantity of sodium chloride is added to the solution so as to have a solution which is 0.5M with respect to NaCl, and 4 volumes of ethanol are then added. The precipitate is allowed to form for 5 minutes at room temperature. The suspension is centrifuged at 5000×g for 20 minutes. The centrifugation pellets are taken up in ethanol, and the suspension obtained is stirred and left standing for 1 hour at room temperature. The centrifugation and suspension operations are repeated. The suspension is centrifuged again at 5000×g for 20 minutes. The centrifugation pellets obtained are dried in an oven under vacuum at 40° C. for 24 hours. The N-acetylheparosan obtained is a "purified high molecular mass N-acetylheparosan". The N-acetylheparosan is then taken up in sterile water so as to have a solution of high molecular mass N-acetylheparosan of concentration 28 g/l.

EXAMPLE 1

Production and Characterisation of the Enzyme

1- Production of an *Escherichia coli* (K5) SEBR 3282 Culture Containing the Enzyme To obtain the enzyme, culturing of *Escherichia coli* (K5) strain SEBR 3282 is performed under environmental conditions favourable to enzyme formation. In effect, it is necessary to use a complex culture medium as described below. However, other equivalent media may be used. Media C and D, whose composition is shown in Table IV below, will be referred to hereinafter as "complex media". 400 ml of medium D are inoculated with *Escherichia coli* strain SEBR 3282 (deposited with the CNCM of the Pasteur Institute, Paris, France, under No. I-1013), and the suspension is incubated with stirring for 2 h at 37° C. The preculture obtained is then transferred to an 18.5-l fermenter containing 11 l of medium C, and the suspension is incubated for 4 h at 37° C. and at a pH equal to 7.4, the oxygen partial pressure being maintained at 40 mmHg by regulating the injection of air (up to 20 l min) and with stirring. Glucose is then added by introducing in continuous fashion a sterile solution containing 600 g/l of glucose at the rate of 250 ml/h for 8 h. Culturing is continued under the same temperature, pH and oxygen partial pressure conditions for 10 h after the addition of glucose has been completed.

Monitoring of the optical density (OD) at $\lambda=600$ mm of the culture medium enables it to be asserted that there is no growth of the biomass during the last 12 hours of culture.

TABLE IV

Composition and preparation of medium C and medium D (COMPLEX MEDIA)

MEDIUM C

Medium C is prepared by combining the three sterile solutions below:

Solution No. 1

In 700 Ml of ultrapurified water, dissolve in order:

| | |
|---|---|
| Complexing agent: N-[Tris(hydroxymethyl)methyl]glycine (Tricine marketed by Fluka ® | 360 mg |
| FeSO$_4$.7H$_2$O | 280 mg |
| CaCl$_2$.2H$_2$O | 6.7 mg |
| MgCl$_2$.6H$_2$O | 1270 mg |
| K$_2$SO$_4$ | 500 mg |
| KCl | 5000 mg |
| Casein hydrolysate (main source of amino acids) HY CASE SF ® (marketed by Sheffield) | 25000 mg |
| Yeast extract (marketed by Difco ®) | 18000 mg |
| Solution of trace elements (see Table II) | 1 ml |

Antifoaming agent Struktol J673 ®(marketed by Schill and Seilacher): a few drops with a Pasteur pipette. Adjust the pH to 7.4 with KOH solution (d = 1.38) and make to 850 ml with ultrapurified water. Autoclave the medium for 45 minutes at 120° C.

Solution No. 2

Dissolve 5 g of K$_2$HPO$_4$ in approximately 40 ml of ultrapurified water and then adjust to 50 ml with the same solvent. Filter the solution obtained through a filter of porosity 0.2 μm.

Solution No. 3

Dissolve 20.7 g of glucose in an appropriate quantity of ultrapurified water and adjust the volume to 100 ml with the same solvent. Autoclave at 110° C. for 30 minutes.

MEDIUM D

The preparation of medium D is identical to that of medium C except that, in addition, 20 g of pH 7.2 buffer (3-morpholinopropanesulphonic acid) should be added after addition of the antifoaming agent. An *Escherichia coli* (K5) culture containing the enzyme which is the subject of the invention is thereby obtained.

2- in vivo Demonstration of the Enzyme in a Fermenter

The in vivo demonstration of the enzyme was accomplished by the induced fragmentation of a quantity of high molecular mass N-acetylheparosan added to a culture suspension possessing eliminase activity.

The aqueous solution of high molecular mass N-acetylheparosan obtained in the preceding stage is added in an 18.5-liter fermenter to an *Escherichia coli* (K5) strain SEBR 3282 culture containing the enzyme when the culture has reached the plateau. This is demonstrated by the monitoring of the OD at $\lambda=600$ nm (1- Production of an *Escherichia coli* (K5) SEBR 3282 culture containing the enzyme).

Samples of culture suspension were taken at 3, 5, 7, 9.75 and 13.5 hours after addition of exogenous N-acetylheparosan, as well as immediately after this addition.

Step A

Determination of the Distribution of Molecular Masses of N-acetylheparosans During the Fermentation The determination of the distribution of molecular masses of the N-acetylheparosans contained in the different samples was performed by exclusion HPLC.

a- Exclusion HPLC operating conditions

Column: TSK G 3000 SW® (LKB) 7.5×300 mm consisting of silica beads 10 μm in diameter and of porosity 250 Å.

Eluent: 0.5M aqueous sodium sulphate solution, filtered through 0.2 μm and degassed.

Flow rate: 1 ml/minute

UV detection at $\lambda=205$ nm calibration is performed using a series of oligosaccharides derived from heparin (10 mg), of the following molecular masses (Da): 1320, 1880, 2440, 3410, 4000, 4540, 5000, 5370, 5730, 6150, 6670, 7540, 8660, 10090, 11560, 12950, 14810, 17390, 22670.

b- Sample preparation

The starting material is a sample taken from the culture suspension in a fermenter. Centrifuge at 7000×g for 2 minutes. Recover the supernatant and filter it through a 0.2 μm membrane, precipitate the filtrate by adding 4 volumes of absolute ethanol, equivalent to a final 80% of ethanol, vortex and wait 5 minutes. Centrifuge at 4000×g for 5 minutes, remove the supernatant, take the pellet up in ultrapurified water to the initial volume, vortex and dialyse using a Spectra-Por® sac (Spectrum) of cut-off threshold 10,000 Da overnight against ultrapurified water.

With magnetic stirring at 4° C., add concentrated NaCl solution such that the final concentration of the solution containing the N-acetylheparosan is 0.5M. Precipitate by adding 4 volumes of absolute ethanol per volume of salted dialysate, and vortex. Wait 5 minutes, centrifuge at 4000×g for 5 minutes, discard the supernatant, take the pellet up in 25 mM piperazine buffer, pH 3.5 so as to obtain a concentration lying between 5 and 10 g of N-acetylheparosan/liter, and vortex strongly.

Deposit the equivalent of 1 mg of N-acetylheparosan on a column of Q Sepharose® resin previously equilibrated with the piperazine buffer, and wash the column of resin with 2 volumes of piperazine buffer. Wash with 4–5 volumes of ultrapurified water, elute with 2 volumes of 0.5M NaCl, collect the eluate and precipitate with absolute ethanol as above.

Centrifuge at 4000×g for 5 minutes, and take the pellet up in ultrapurified water so as to obtain a concentration lying between 5 and 10 g/l of N-acetylheparosan.

This solution is ready for the determination of the distribution of molecular masses by exclusion chromatography.

Figure 1:
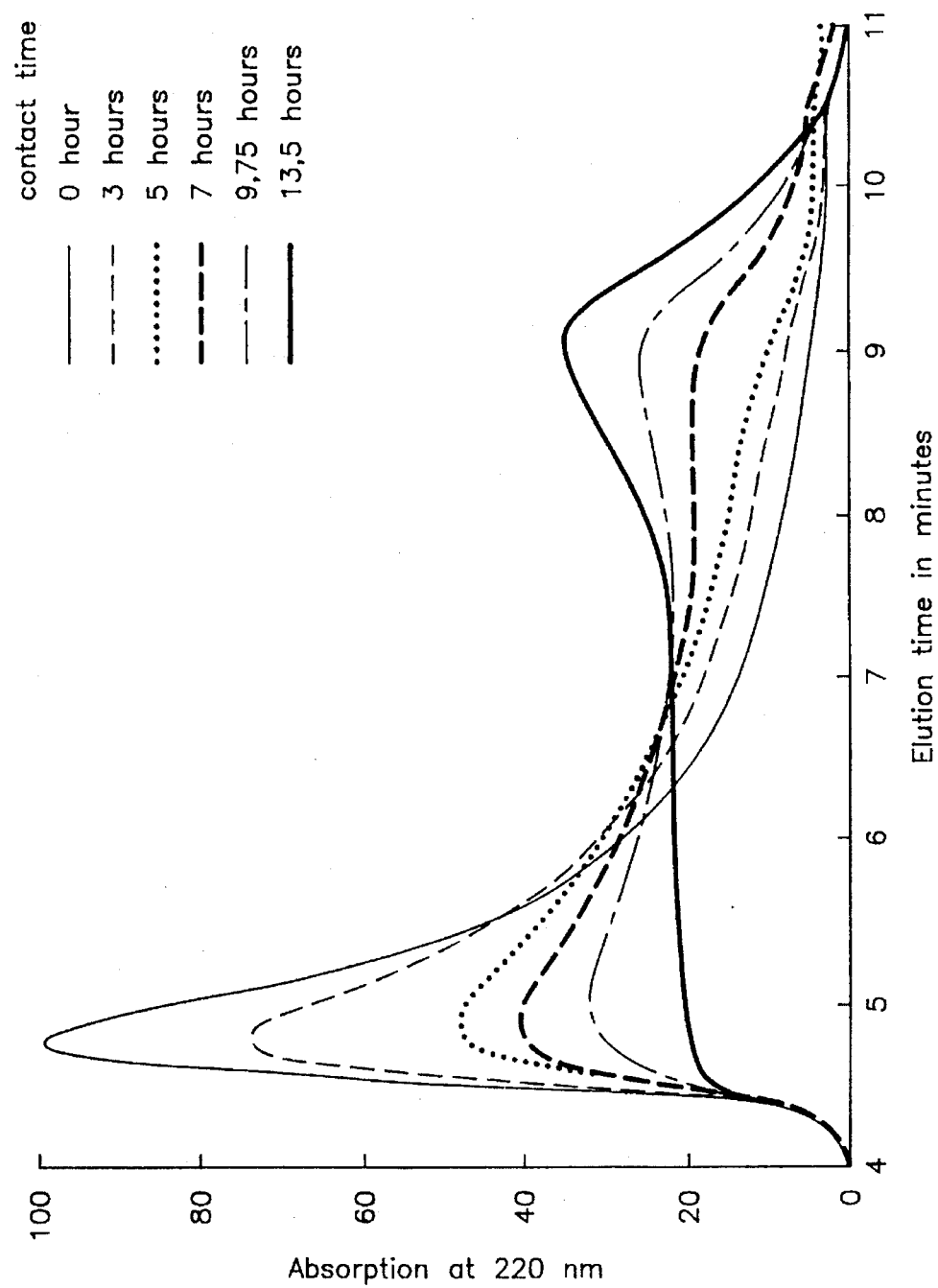
FIG. 1 is a graph showing in vivo fragmentation of different classes of N-acetylheparosans in a fermenter at different times.

The results corresponding to the samples analysed are given in the form of chromatographic profiles in FIG. 1.

From these data, the N-acetylheparosan fragments were divided into three classes:

Fragments having a molecular mass of greater than 100,000 Da

Fragments having a molecular mass of between 5000 and 100,000 Da

Fragments having a molecular mass equal to approximately 5000 Da.

Figure 2:
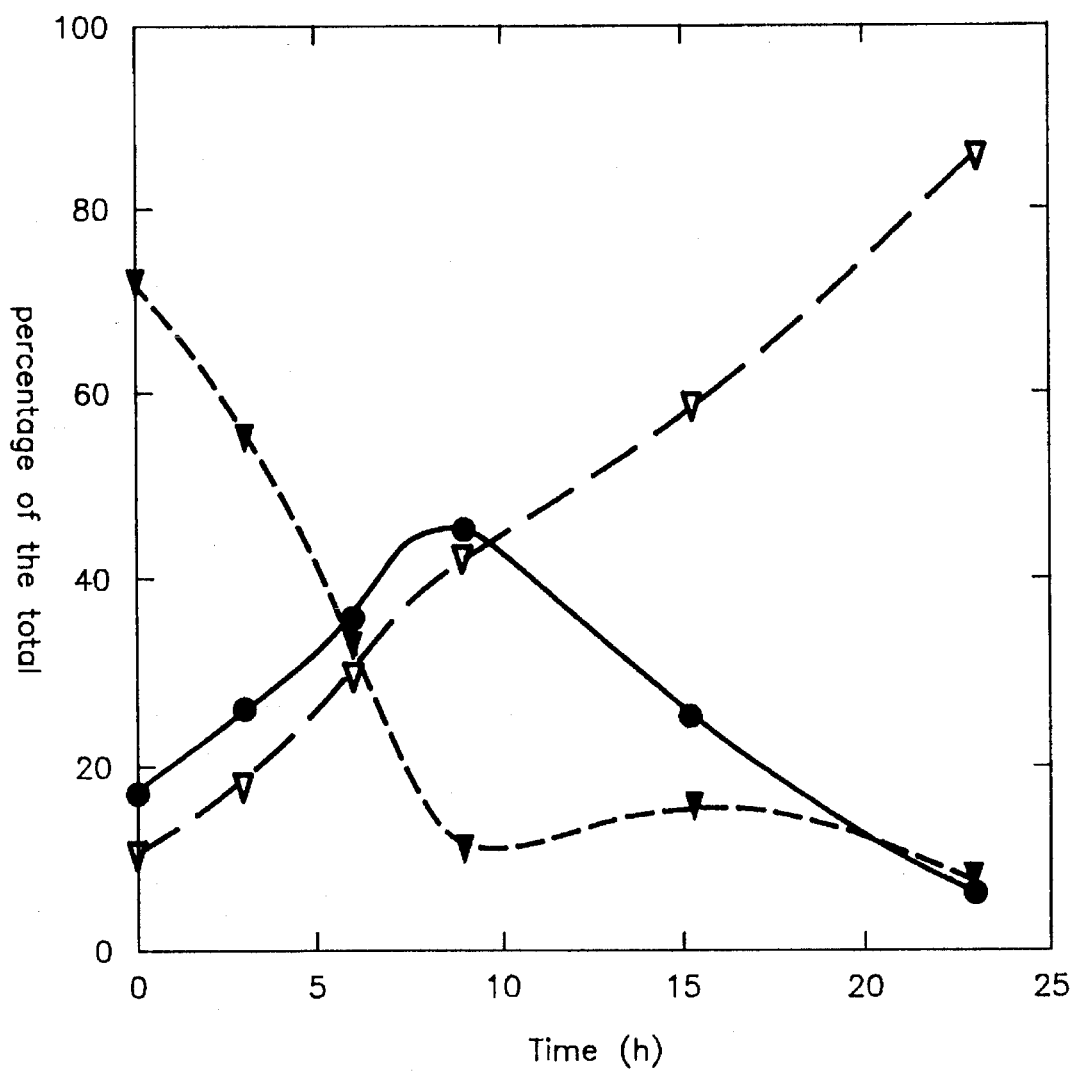
FIG. 2 is a graph showing the relative abundance of the different classes of N-acetylheparosans as a function of time.

The relative abundance of 3 classes of fragments in the fermenter as a function of time is shown in FIG. 2.

Examination of FIG. 1 permits the following conclusions:

The high molecular mass N-acetylheparosan of the culture and that which was added thereto gradually change into N-acetylheparosan predominantly of low molecular weight.

Examination of FIG. 2 permits the following conclusions:

There are transient steps in which N-acetylheparosan of intermediate molecular mass is detected, that is to say the whole range of molecular masses is represented at the same time. However, after 24 hours, the high molecular mass N-acetylheparosan introduced into the fermenter is fragmented virtually completely (80%) into fragments having a molecular mass of approximately 5000 Da.

The fragmentation is hence performed on exogenous N-acetylheparosan either by enzymes in solution, or in contact with membrane enzymes.

Step B

Verification of the Structure of the Low Molecular Mass N-acetylheparosans obtained by NMR The proton and carbon $^{13}$C NMR spectra of the N-acetylheparosans obtained after enzymatic fragmentation are compared with those of N-acetylheparosan which are described by W. E. Vann (Eur. J. Biochem., 1981, 116, 359–364).

A study of the spectra obtained with the low molecular mass (approximately 5000 Da) N-acetylheparosans confirms the chemical identity of the product with the N-acetylheparosan described by W. E. Vann. The compound comprises polymer chains consisting of repeated β-D-glucuronyl(1→4)-N-acetyl-α-D-glucosaminyl-(1→4) structures.

Furthermore, these same spectra enable it to be concluded that the fragments contain at the non-reducing end a glucuronic acid residue having a double bond between carbons 4 and 5.

The results obtained clearly indicate that the enzyme responsible for the fragmentation is of the β-eliminase type, by virtue of the presence of a double bond at the non-reducing end of the low molecular mass N-acetylheparosan obtained, this end being a glucuronic acid residue.

Moreover, this enzyme makes it possible to obtain, at the end of culturing, from a high molecular mass N-acetylheparosan, a majority of fragments having identical sizes which correspond to a molecular mass of approximately 5000 Da. Hence the enzyme of the invention must be capable of interacting with the N-acetylheparosan macromolecule at a given distance from the end of this macromolecule. This enables fragments consisting of a very precise number of "β-D-glucuronyl-(1→4)-N-acetyl-α-D-glucosaminyl-(1→4)" units to be obtained. The enzyme is hence an endo-β-eliminase.

3- Localisation of the Enzyme - Production of Preparations Containing this Enzyme The main steps shown in Scheme 1, which steps have made it possible to obtain preparations containing the enzyme, and in particular a crude lysate and a membrane preparation having enzymatic activity, are illustrated below.

Step A

Production of a Crude Lysate Possessing Enzymatic Activity. Assessment of its Activity a- Preparation of a crude lysate The crudelysate possessing enzymatic activity was prepared from the pellet of an *Escherichia coli* (K5) strain SEBR 3282culture suspension containing the enzyme (1-Production of an *Escherichia coli* (K5) strain SEBR 3282 culture containing the enzyme), in the following manner:

After incubation, the culture medium is cooled to 25° C. and then subjected to a centrifugation (31,000×g) for 15 minutes. To 200 g of wet pellets, 400 ml of 50 nM Tris-HCl buffer, pH 8 and an appropriate quantity of EDTA so as to obtain a final concentration of 10 mM are added. 100 mg of lysozyme are then added.

The enzymatic reaction performed with lysozyme is carried out at room temperature, the pH being maintained at 8.0. When the mixture is homogeneous, it is placed at 4° C. overnight. After this time interval, the pH is readjusted to 7.5 and $MgCl_2$ is added to a final concentration of 20 mM, followed by DNase I®, 15 mg in total.

b- Demonstration of the fragmentation produced by the crude lysate

Using the crude lysate described above, an in vitro fragmentation of a high molecular mass N-acetylheparosan was observed using the following procedure:

The pH of the crude lysate is adjusted to 6.8. 600 µl are withdrawn, and 1 mg of purified high molecular mass N-acetylheparosan, as described in the PREPARATION is added thereto. The mixture is then incubated at 37° C. for 24 hours. When the reaction is complete, the distribution of molecular masses of the N-acetylheparosan obtained is carried out.

The determination of the distribution of molecular masses of the samples was performed by exclusion HPLC as described above (2- In vivo demonstration of the enzyme in a fermenter - Step A).

Figure 3:
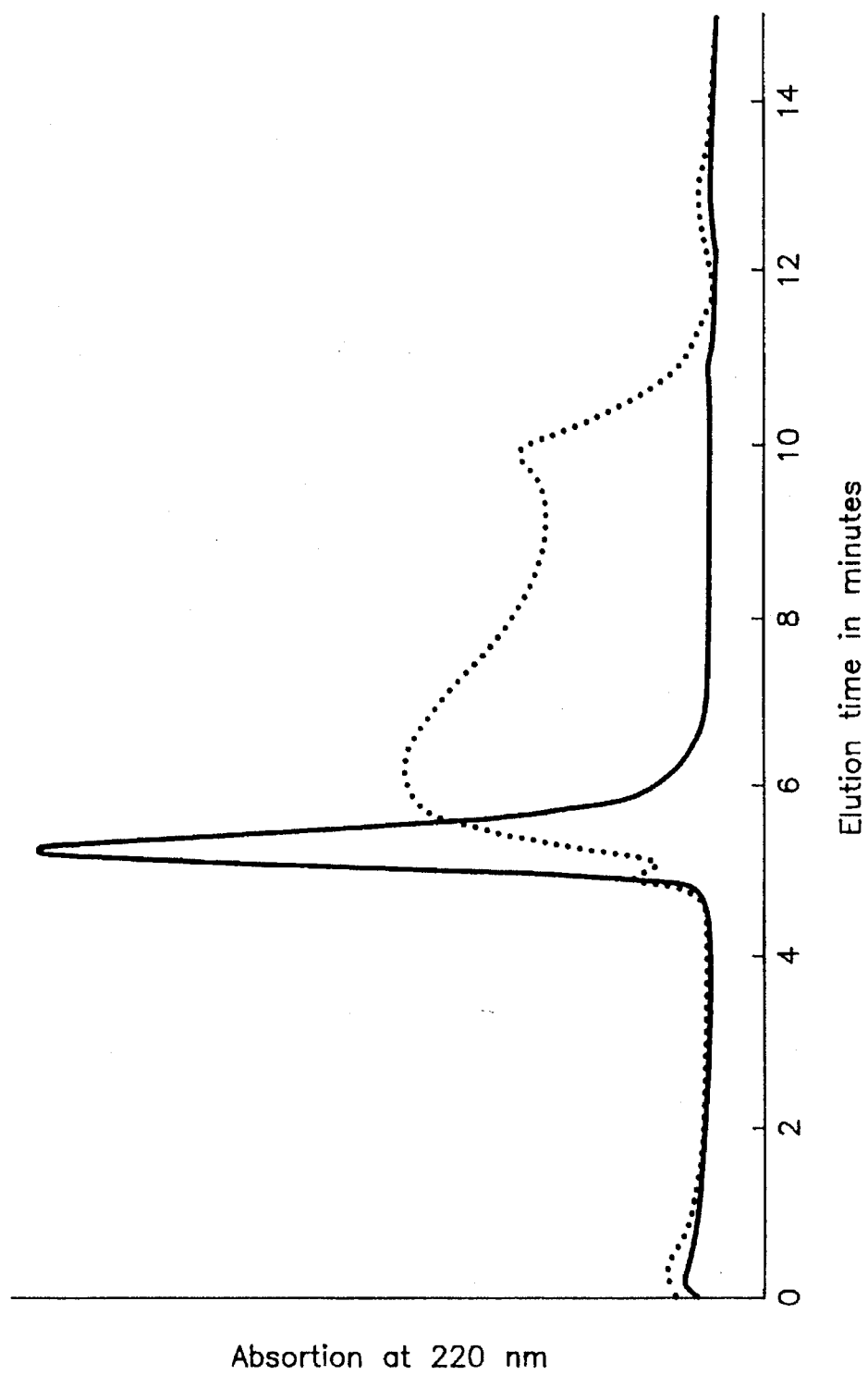
FIG. 3 is an in vitro demonstration of the endo-β-eliminase activity of a high molecular mass N-acetylheparosan.

A high molecular mass N-acetylheparosan control without lysate was also treated under the same conditions. Comparison of the chromatographic profiles obtained demonstrates that no fragmentation of the control has taken place (FIG. 3 - broken lines). It is still a high molecular mass N-acetylheparosan composed of constituents having molecular masses ranging from 10,000 to 100,000 Da.

In contrast, a fragmentation is observed when the high molecular mass N-acetylheparosan is treated with the crude lysate. On the chromatographic profile, fragments are observed having a molecular mass of between approximately 4000 and 8000 Da, with a peak eunassing fragments of approximately 5000 Da corresponding to the major part of the final product (FIG. 3 - continuous lines).

The β-eliminase type enzymatic activity of the strain SEBR 3282 may hence be exploited in the absence of bacterial particles, in vitro, using a simple crude lysate. It is also highly surprising that the fragments are not split below a certain size, in contrast, for example, to what is obtained with the phage lyase specific for the strain *Escherichia coli* (K5), which effects the total disappearance of the 5000-Da fragments in favour of much smaller entities (Gupta D., Jann B and Jann K; FEMS Microbiology Letters 1983 16, p. 13–17).

Step B

Production of a Membrane Preparation Possessing Enzymatic Activity - Assessment of its Activity The crude lysate obtained in the preceding step is subjected to a centrifugation at 15,000×g for 60 minutes. The pellet is removed and the supernatant is centrifuged at 105,000×g for 60 minutes. The pellet containing the bacterial membranes is isolated and taken up in the initial volume with purified water.

Demonstration of the eliminase activity of this membrane preparation is performed as described in the preceding step, incubating an aliquot of this preparation brought into contact with high molecular mass N-acetylheparosan at a pH in the region of neutrality and at a temperature of 37° C. After one night, a sample is withdrawn and the assessment of the distribution of its molecular mass is performed by HPLC using the method quoted above (2- In vivo demonstration of the enzyme in a fermenter - Step A). The results obtained show that the endo-β-eliminase enzymatic activity occurs in the bacterial membranes. This does not rule out, as indicated in Scheme 1, the possibility of detecting an activity in the supernatant of the culture suspension, obtained after low-speed centrifugation (15,000×g). In effect, a partial lysis of the bacteria takes place spontaneously, after the plateau phase, within the culture suspension.

4- Solubilisation of the Enzyme 4.1- Solubilisation Using Detergents

As a result of the techniques for assay of enzymatic activity which necessitate a functional enzyme, the detergents in question were chosen predominantly from nonionic and non-denaturing detergents (Schütte H, Kula M. R; Biotechnology and Applied Biochemistry (1990), 12, 559–620).

Solubilisation of the enzyme in membrane form was performed using a membrane pellet as described above (3-Localisation of the enzyme - Production of preparations containing this enzyme - Step B).

The membrane pellets are taken up in a solution of detergents of the same volume as the initial crude lysate, and the mixture is then left in contact overnight at 4° C. It is then subjected to a centrifugation at 105,000×g for 1 hour. The supernatant containing the proteins is recovered, dialysed and passed through an affinity column for detergents, according to the directions of the supplier.

Demonstration of the activity of the different preparations containing the enzyme in soluble form was performed by incubating an aliquot of the high molecular mass preparations at a pH in the region of neutrality and at a temperature of 37° C.

After 6 days of incubation, samples are withdrawn and the distribution of molecular masses of the N-acetylheparosans obtained is assessed by HPLC according to the method described above. The results of this study are collated in Table V.

A portion of the membrane pellet, taken up in 50 nM Tris-HCl buffer, pH 8, served as control. The latter was treated under the conditions quoted above.

Assay of total proteins was performed using "BCA protein assay reagent" of Pierce®.

The results shown in Table V demonstrate that, apart from the sample treated with guanidine thiocyanate, under the operating condinions shown, the enzyme preparations solubilised with detergents are active provided the detergent concentration of the aqueous solution is lowered after solubilisation of the enzyme.

In effect, the control after 6 days of incubation at 37° C. exhibits only a slight attack of N-acetylheparosan, of the order of 10%, whereas in the other tests, the fragmented N-acetylheparosan of low molecular mass represents approximately 90% of the initial mass, this being a maximum.

TABLE V

| TEST | MEMBRANE PROTEINS IN g/l IN SOLUBLE FORM | DEGREE OF SOLUBILIS-ATION*/ MEMBRANE PROTEINS | ENDO-β-ELIM-INASE ACTIV-ITY |
| --- | --- | --- | --- |
| 1. Tris-HCl control | 0.32 | 17% | SLIGHT |
| 2. Triton x-100 ®, 2% | 0.88 | 44.5% | STRONG |
| 3. Triton X-114 ®, 2% | 1.64 | 68.6% | STRONG |
| 4. DOC, 2% | 0.86 | 55.1% | STRONG |
| 5. NP-40 ®, 2% | 0.97 | 58.0% | STRONG |
| 6. GUANIDINE THIOCYANATE 4M | 2.72 | 90.7% | NIL |
| 7. Tween 80 ®, 2% | 0.57 | 24.1% | STRONG |
| 8. Guanidine HCl, 0.1 M | 1.04 | 58.4% | STRONG |

Another fact of interest which becomes apparent when the chromatographic profiles are superposed is the shifting of the peak amassing the N-acetylheparosan fragments predominantly of low molecular masses of 5000 Da. For the membrane enzyme (control), it lies at around 5000 Da. For the sample treated with Triton X-114®, it lies at around 6500 to 7000 Da (according to heparin standard).

A study of the solubilisation of the enzyme enables it to be concluded that:

the enzyme may be solubilised by a large number of detergents and obtained in active form;

the soluble form of the enzyme makes it possible to obtain peaks representing an aggregate of a majority of N-acetylheparosan fragments around a molecular mass (top of the peak) higher than that observed for the membrane form of the enzyme.

4.2 - Solubilisation by Alkaline Lysis

Solubilisation of the enzyme by alkaline lysis was performed using a crude bacterial pellet. The crude bacterial pellet was obtained by centrifugation of the culture medium at 10,000×g for 10 minutes (3- Localisation of the enzyme - Production of preparations containing this enzyme - Step A).

The bacterial pellet was frozen at −20° C. 180 g of this bacterial pellet are suspended in 100 ml of ultrapurified water, and the pH of the suspension is adjusted to 11 using concentrated sodium hydroxide solution. The alkaline suspension is maintained at pH 11 and at 4° C. for 2 hours. The lysate thereby obtained is ultracentrifuged at 105,000×g for one hour. The supernatant is recovered, the pH is adjusted to 7 and the mixture is then dialysed at 4° C. overnight in a sac of cut-off point 10,000 against 10 liters of ultrapurified water (water flow rate 90–120 ml/hour). A portion of the lysate thereby obtained is stored at 4° C., and another at −80° C.

To determine the enzymatic activity, 500 µl of high molecular mass N-acetylheparosan (PREPARATION) were incubated for 15 hours at 37° C. with 125 µl of the lysate obtained and stored either at 4° C. or at −80° C. Determination of the molecular mass of N-acetylheparosan obtained after incubation demonstrated that the activity of the lysate obtained by alkaline lysis is strong. The storage conditions do not appear to have an important role, since the same activity was observed with the lysate stored at 4° C. and with that stored at −80° C.

A study of the solubilisation of the enzyme enables it to be concluded that:

solubilisation of the enzyme by alkaline lysis and ultracentrifugation enables a β-eliminase type activity to be obtained which is of the same order as that resulting from the action of detergents;

transitory freezing of the lysate at −80° C. does not give rise to any loss of enzymatic activity.

5- Determination of the Isoelectric Point (pHi) of the Solubilised Enzyme

Determination of the pHi of the eliminase is carried out by means of the chromatofocusing method. The principle of this is to create a pH gradient across a chromatography column. The proteins are then eluted when their charges are overall neutral (at their pHi). The pH range tested is between pH 3.5 and pH 9.

a- Equipment used

Low pressure column: 10×30 cm (Pharmacia®)

PBE 94 gel (Pharmacia®)

Eluent: Polybuffer 96 and Polybuffer 74 (Pharmacia®)

Starting buffer for 6< pH<9 : 0.025M diethanolamine-HCl, pH 9.5

Starting buffer for 3.5<pH<6: 0.025M histidine-HCL, pH 6.2

Pump: Gilson®.

b- Production of solubilised eliminase 4 g of wet, membrane pellets are introduced into 10 ml of 0.1M Tris-HCl buffer, pH 10.5 containing 0.3M $CaCl_2$. The solubilisation operation takes 2 hours at room temperature. The suspension is then centrifuged at 105,000×g for 1 hour. The supernatant containing the enzyme is at a concentration of 3 mg/ml of active proteins.

Initially, the pH range chosen lay between pH 6 and 9. More accurate results were obtained by repeating the tests and using a pH range between 4.7 and 5.4.

The enzymatic activity of the different fractions was assessed by bringing the fractions obtained during the gradient chromatography into contact with a high molecular mass N-acetylheparosan, and determining the distribution of molecular masses of the N-acetylheparosan obtained after incubation for 60 hours at 37° C. and at pH 6.8.

The phi of the enzyme is between pH 4.7 and pH 5.4.

Figure 4:
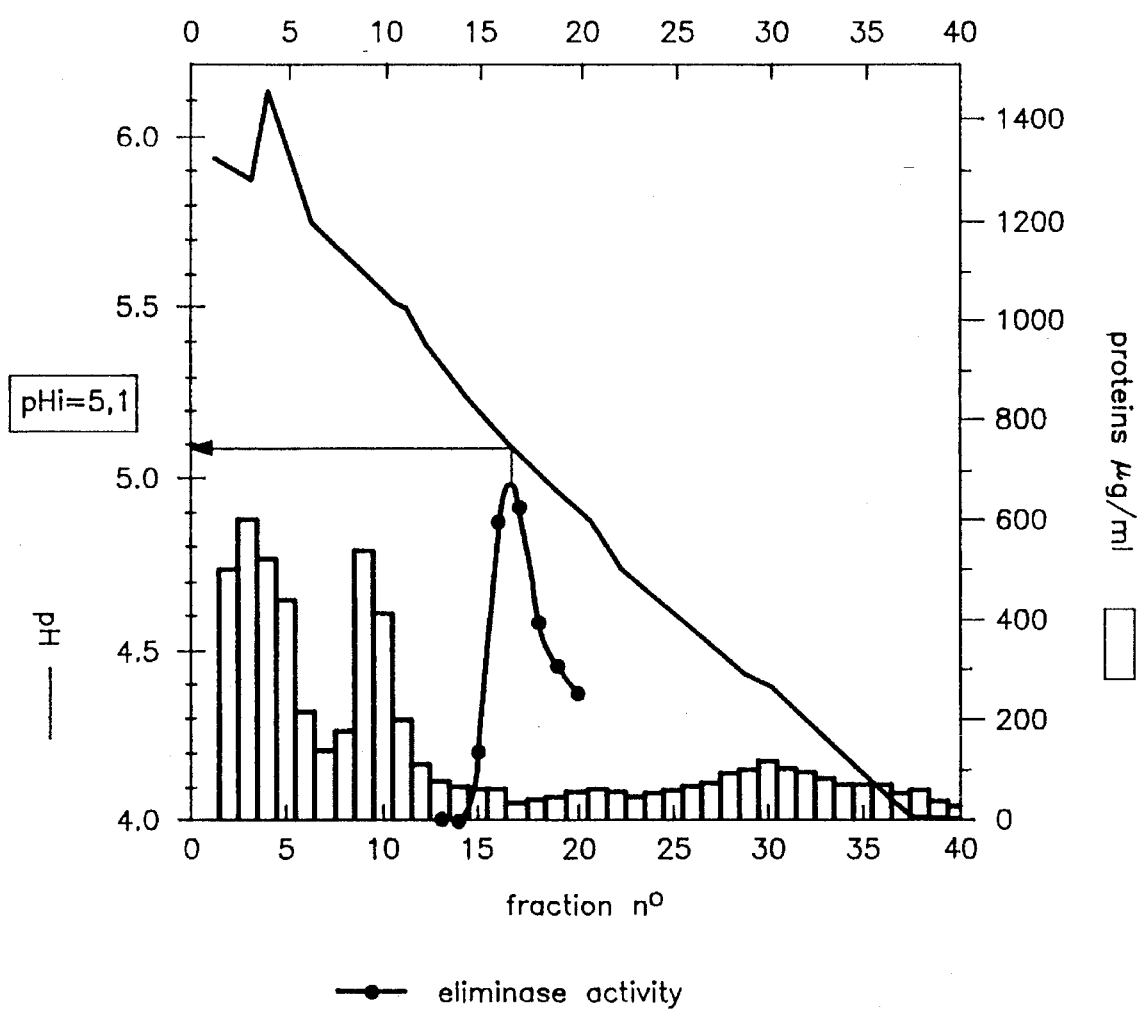
FIG. 4 shows the determination of the pH of the eliminase enzyme using chromatofocusing.

Further chromatofocusing experiments were undertaken in order to define the phi of the enzyme more precisely. Maximal activity was found in a fraction of pH 5.1. The phi of the eliminase is consequently 5.1 (FIG. 4).

6- Determination of the Molecular Mass of the Solubilised Enzyme

Test 1

Determination of the molecular mass of the eliminase was performed by gel permeation chromatography (GPC). The proteins are eluted as a function of their molecular mass, the smallest sizes emerging first.

a- Equipment used

Column: TSK G 2000 SW®, 7.5×300 mm

Eluent: 0.3M NaCl/50 mM Tris, pH 7

Flow rate: 0.3 ml/minute

Figure 5A:
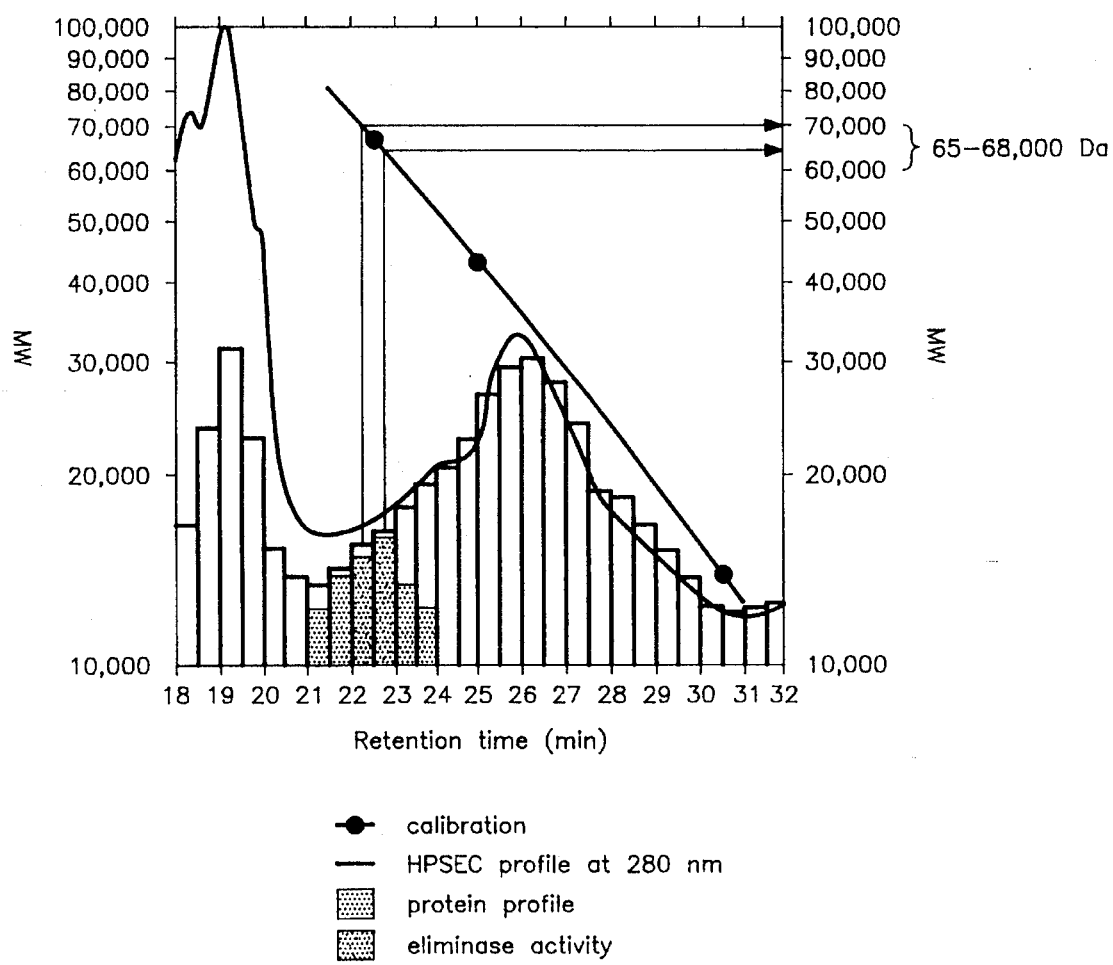
FIG. 5a shows a graph of molecular mass of the eliminase using gel permeation chromatography.

Detection at 280 nm with a sensitivity of 0.2 AUFS b- Production of solubilised eliminase 4 g of wet membrane pellets are introduced into 10 ml of 0.1M Tris-HCl buffer, pH 10.5 containing 0.3M calcium chloride. Solubilisation takes 2 hours at room temperature. The suspension is then centrifuged at 105,000×g for 1 hour. The supernatant containing the enzyme is at a concentration of 3 mg/ml of active proteins. 24 fractions collected every 30 seconds were obtained. The enzymatic activity of the different fractions obtained was assessed by bringing each fraction into contact with a high molecular mass N-acetylheparosan. After incubation for 38 hours at 37° C. and at pH 7, the distribution of molecular masses of the N-acetylheparosan obtained was determined. The most active fractions lie at between 22 and 23 minutes (FIG. 5a). On the basis of the two highest peaks with respect to eliminase activity, the molecular mass of the eliminase lies between 62,000 and 70,000 Da, and more precisely at about 65,000 Da. The initial suggestion is hence that the eliminase has a molecular weight lying between 62,000 and 70,000 Da, and more especially at about 65,000 Da.

Test 2

Figure 5B:
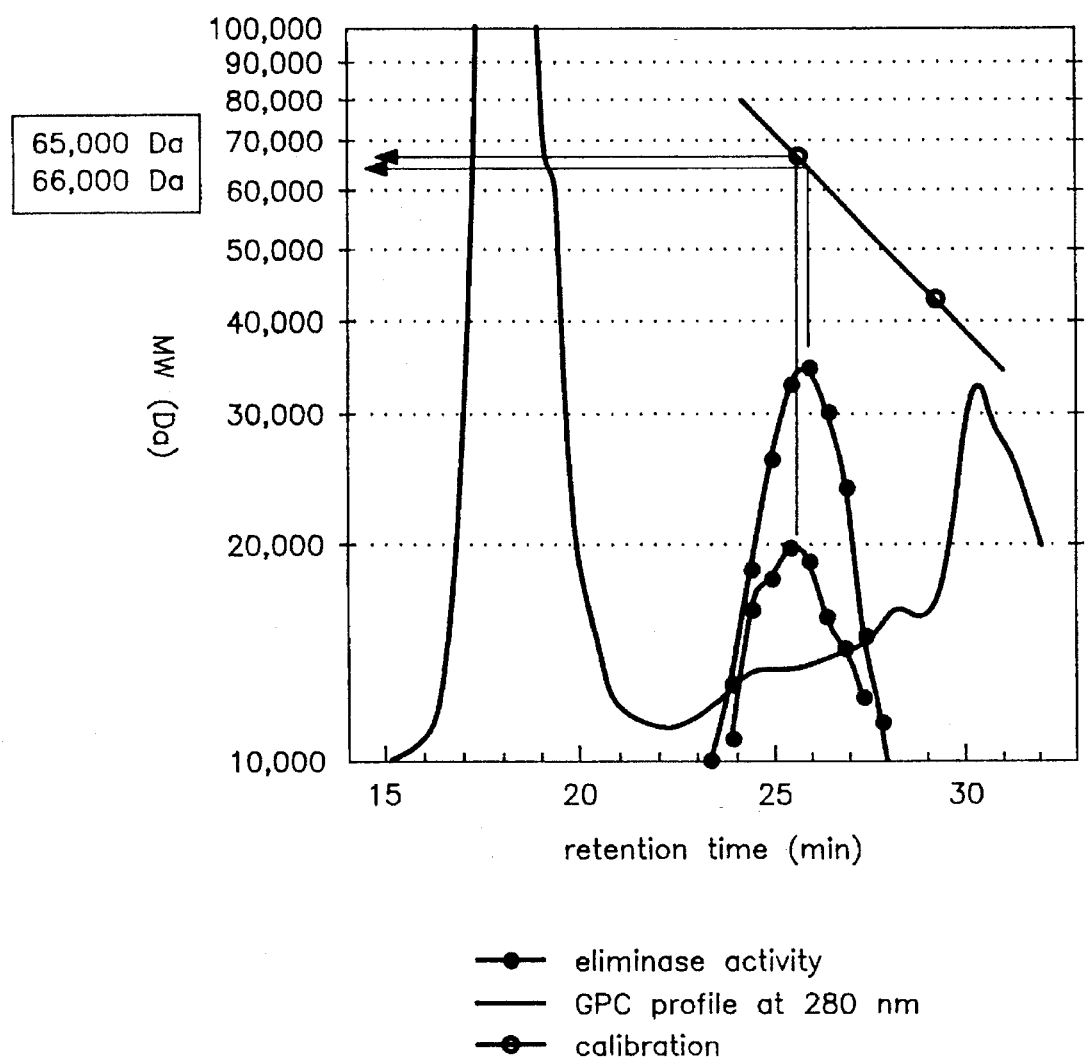
FIG. 5b shows a graph of molecular mass of the eliminase using a chromatography column.

In order to define the molecular mass of the enzyme more precisely, an additional test was carried out using a chromatography column, TSK G 3000 SW® column, 7.5×300 mm. This column permits a better separation of molecular masses of approximately 100,000 Da. The technique used and the operating conditions are identical to those described in Test 1. The calibration includes molecular masses of 43,000 Da and 67,000 Da. In this test, it is observed that the retention times of the fractions having maximal activity of the enzyme correspond to molecular masses of 65,000 Da to 66,000 Da (±1500 Da) (FIG. 5b).

7- Environmental Factors Exerting an Incluence on the Activity of the Enzyme - Membrane Preparation For this study, a membrane preparation as described above (3- Localisation of the enzyme - Step B - Production of a membrane preparation possessing enzymatic activity. Assessment of its activity) was used. The enzymatic activity of this preparation, observed according to the different parameters studied, was assessed by determining the dispersion of molecular masses of a high molecular mass N-acetylheparosan subjected to its action.

a- Temperature

The optimal temperature of functioning of the enzyme is in the region of 37° C., its inactivation temperature is 60° C., and at 20° C. the enzyme retains 40% of its activity in comparison to that at 37° C.

b- pH

The optimal range of functioning of the enzyme lies between the values pH 6 and pH 7. At pH 5 and at pH 7.5, the enzyme retains 40% of its activity in comparison to that observed in the range pH 6–7. At pH 8.5, the enzyme retains less than 10% of this activity.

c- Effect of monovalent ions ($Na^+$)

The optimal range of concentration of sodium ions for the functioning of the enzyme lies in the vicinity of 0.2M. At this concentration of monovalent ions, the activity of the enzyme increases by approximately 15% relative to the control. It should be noted here that sodium ions enable the top of the peak of the N-acetylheparosan fragments to be shifted towards the high molecular masses. The membrane enzyme placed under these conditions generates fragments of molecular mass approximately 500 Da higher than those of the control.

Some monovalent ions, especially sodium, hence enable the size of the fragments obtained at the end to be varied.

d- Effect of divalent ions ($Ca^{2+}$)

The optimal range of concentrations of calcium ions for the functioning of the enzyme lies in the vicinity of 0.2M. With this concentration, the activity of the enzyme increases by approximately 50% relative to the control.

e- Michaelis constant

Measurement of the fragmentation reaction as a function of the concentration of substrate (in this case high molecular mass N-acetylheparosan) enables it to be established, after a Lineweaver-Burk plot:

that a straight line is obtained; the enzyme hence obeys Michaelis kinetics;

that the Michaelis constant is equal to the substrate concentration for which the reaction rate is half the maximal rate, and is practically equal to 1 g of N-acetylheparosan/liter of reaction solution;

that high substrate concentrations, for example 30 g/l, at and above which the N-acetylheparosan solution begins to become viscous, do not constitute an appreciable obstacle to the good functioning of the enzyme.

f- Stability of the enzyme

Influence of pH:

After a change to pH 10.5 at which the enzyme is inactivated, the enzyme recovers its activity once it has returned to pH values close to neutrality. The enzyme also withstands a change to pH 3.5.

Influence of temperature - Storage at 4° C.:

After storage at 4° C. for 3 months, no significant loss of activity is observed in regard to the enzyme.

Influence of a reducing agent:

The presence of dithioerythritol (DTE) exerts a stabilising influence on the activity of the enzyme.

8- Environmental Factors Exerting an Influence on the Activity of the Enzyme - Crude Bacterial Pellet The crude bacterial pellet, which can be obtained after centrifugation of the culture medium at 10,000×g for 10 minutes, may also be used to fragment high molecular mass N-acetylheparosan for preparatory purposes. The conditions for using crude bacterial pellets, previously induced in order to have enzymatic activity with the object of fragmenting high molecular mass N-acetylheparosan, were studied.

a- Temperature

The temperature of maximal enzymatic activity of the pellet is in the region of 40° C. The pH interferes slightly with the effect of temperature on this product.

b- pH

The optimal range of enzymatic activity of the pellet lies between the values pH 6.6–6.8. At pH 7.5, the enzyme retains 40% of its maximal activity.

c- Effect of monovalent ions ($Na^+$)

Among the monovalent ions studied, , $Na^+$, $K^+$ and $Li^+$ in the form of salts (chlorides), the $Na^+$ ion exerts the greatest activating effect on the enzymatic activity of the crude bacterial pellet. The maximal activating effect is observed when the concentration of $Na^+$ ions is approximately 0.3M.

d- Effect of divalent ions ($Ca^{2+}$)

Among the divalent ions studied, $Ca^{2+}$ and $Mg^{2+}$ in the form of salts (chlorides), $Ca^{2+}$ ion exerts the greatest activating effect on the enzymatic activity of the crude bacterial pellet. The optimal range of concentration of calcium ions lies at 0.1–0.15M. Under these conditions, the activity of the enzyme is multiplied twofold.

Divalent metal ions such as $Zn^{2+}$ and $Cu^{2+}$ proved to be more or less inhibitory of this enzymatic activity.

e- Michaelis constant

As a result of the characteristics of the crude preparation, the kinetic study carried out on the enzyme linked to the bacterial particles is interpreted with reservation. However, it was established that:

the enzymatic activity of the crude bacterial pellet shows Michaelis type behaviour, like the enzyme obtained in membrane form (membrane preparation);

the Michaelis constant under the optimal conditions (temperature, pH, $Ca^{2+}$ ion concentration) is of the order of 2.2 to 3.2 g of N-acetylheparosan per liter of reaction solution.

The Michaelis constant for the crude bacterial pellet is hence markedly higher than that found for the membrane preparation.

f- Competitive inhibitors of the enzyme/substrate interaction

It was observed that N-acetylglucosamine and glucuronic acid, both of which are components of N-acetylheparosan, are competitive inhibitors of the enzymatic activity of the crude bacterial pellet.

g- Modification of the substrate

The carboxyl and N-acetyl groups of N-acetylheparosan were removed with 1-ethyl-3-(3-dimethylaminopropyl)carbodiimide hydrochloride (EDC) and sodium hydroxide in the heated state. This polymer, deprived of one or other of these groups, is no longer attacked by the enzyme.

h- Stability of the enzymatic activity of the pellet
Influence of temperature

The bacterial pellet may be stored at −20° C. or −80° C. without significant loss of its eliminase activity.

9- Study of the Kinetics of Fragmentation of N-Acetylheparosan by the Enzyme - Crude Bacterial Pellet To study the kinetics of fragmentation of N-acetylheparosan by the enzyme contained in the crude bacterial pellet, a sample of high molecular mass N-acetylheparosan was brought into contact with an eliminase-rich *Escherichia coli* (K5) SEBR 3282 bacterial pellet at 40° C. in the presence of 140 mM $CaCl_2$ and 50 mM bis-tris propane buffer, pH 6.6. At the end of the enzymatic reaction, a fragmentation of the N-acetylheparosan of the order of 90% was observed. In effect, 90% of the high molecular mass N-acetylheparosan was converted to low molecular mass heparosan. The fragmented N-acetylheparosan was recovered, brought into contact again with a "fresh" crude bacterial pellet and incubated again at 37° C. At the end of this operation, a sample of N-acetylheparosan was withdrawn and purified according to the conditions described in "1- Production of an *Escherichia coli* (K5) SEBR 3282 culture containing the enzyme - Step A - Determination of the distribution of molecular masses of N-acetylheparosan during the fermentation; b- Sample preparation".

The molecular masses of this sample were then assessed by ion exchange HPLC.

Ion Exchange HPLC Operating Conditions

HPLC for producing binary gradients (2 pumps)
Column: Pharmacia® Mono Q® HR 5/5, volume 1 ml
Detector: UV at 220 nm
Eluent: Ultrapurifiedwater (A)
0.5 M aqueous NaCl solution (B)
Use a gradient:

| TIME (MIN) | % of B |
|---|---|
| 0→2.00 | 30.00 |
| 15.00 | 60.00 |
| 17.00 | 100.00 |
| 19.00 | 100.00 |
| 20.00→25.00 | 30.00 |

Flow rate: 1 ml/minute
calibration is performed using a series of oligosaccharides derived from N-acetylheparosan, consisting of 6 to 14 disaccharide units.

The results obtained confirmed that the fragmentation of high molecular mass N-acetylheparosans into low molecular mass N-acetylheparosans is virtually total (≧90%).

The predominant peaks of the fragments of which the low molecular mass N-acetylheparosan is composed correspond to fragments of 8 to 12 disaccharide units.

Hence the molecular mass of the low molecular mass N-acetylheparosan fragments is not modified by a further provision of eliminase. These results confirm that the enzyme enables a virtually complete fragmentation of a high molecular mass N-acetylheparosan to be performed, and fragments having a molecular mass of approximately 5000 Da or slightly less to be obtained.

EXAMPLE 2

Variation-controlled Fragmentation of a High Molecular Mass N-acetylheparosan - Production of an N-acetylheparosan of Molecular Mass of Approximately 7000 Da Stage A Mix 25 g of high molecular mass N-acetylheparosan, obtained according to the PREPARATION, with an enzyme preparation solubilised with a detergent or alternatively by alkaline lysis (Example 1: 4- Solubilisation of the enzyme; 4.2 Solubilisation by alkaline lysis), obtained from 500 g of fresh bacterial pellet which is itself obtained according to Example 1 (1- Production of an *Escherichia coli* (K5) SEBR 3282 culture containing the enzyme. The pH is adjusted to 7 using 0.05M Tris-HCl buffer, pH 7.

Add an appropriate quantity of $CaCl_2$ so as to obtain a final concentration of 0.2M. Incubate at 37° C. for 24 hours.

Stage B

Centrifuge the mixture obtained for 5 minutes at 4000×g. Recover the supernatant and filter it through a 0.2 μm membrane. Precipitate the filtrate by adding 4 volumes of absolute ethanol, equivalent to a final 80% of ethanol. Centrifuge at 4000×g for 5 minutes, remove the supernatant and take the pellet up in ultrapurified water. Dialyse using a Spectra-Por® sac (Spectrum) of cut-off threshold 10,000 Da overnight against ultrapurified water.

With magnetic stirring at 4° C., add concentrated sodium chloride solution such that the final concentration is 0.5M, before precipitating by adding 4 volumes of absolute ethanol per volume of salted dialysate. Centrifuge at 400×g for 5 minutes and discard the supernatant.

Take the centrifugation pellets up in a buffer referred to as buffer D, of composition 20 mM Tris-HCl, pH 7.5, in the proportion of 100 ml/g. The solution obtained is chromatographed on a strong anion exchange column containing an agarose matrix crosslinked with quaternary ammonium groups (Pharmacia® "Q Sepharose fast flow"), previously equilibrated with buffer D in the proportion of 50 ml of gel per g of powder. Wash the gel with a sufficient quantity of buffer D for a return to the base-line of UV detection at 214 nm, and then with a 25 mM solution of piperazine whose pH has been adjusted to 3.5. Elute with a solution of pH 3.5 having the composition: 0.5M NaCl and 25 mM piperazine. The eluate is neutralised using 5M NaOH solution.

Precipitate by adding 4 volumes of ethanol. Centrifuge at 4000×g for 5 minutes. Recover the centrifugation pellet and dry. An N-acetylheparosan consisting of chains the majority of which have a molecular mass of between 6000 and 8000 Da is thereby obtained.

EXAMPLE 3

Variation-controlled Fragmentation of High Molecular Mass N-acetylheparosan Bound to a Column of Anion Exchange Resin in the Presence of the Enzyme which is the Subject of the Present Invention A mass of Q Sepharose® resin (Pharmacia) is initially saturated with N-acetylheparosan predominantly of high molecular mass as described in the PREPARATION. A membrane enzyme preparation, dissolved in a Tris-HCl buffer, pH 7.2 and containing 0.25M sodium chloride, is then introduced. The latter solution was prepared from a crude lysate as described in Example 1 (3- Localisation of the enzyme - Production of preparations containing this enzyme - Step B), but using a Tris-HCl buffer, pH 7.2 containing 0.25M sodium chloride instead of ultrapurified water.

Reaction is allowed to take place for 60 hours. The N-acetylheparosan released as a result of the presence of 0.25M NaCl is isolated and analysed. It is an N-acetylheparosan in which the majority of the chains have a molecular weight of between 3200 and 4000 Da. On the chromatographic profile representing the distribution of molecular masses, the maximum lies at 3600 Da.

The N-acetylheparosan bound to the resin is then eluted using 0.30M aqueous NaCl solution. A study of the chromatographic profile representing the distribution of molecular masses enables it to be confirmed that the maximum lies at 4300 Da. This product is an N-acetylheparosan consisting of chains longer than those of the N-acetylheparosan released.

According to another variant, it is possible to proceed as above but using a membrane enzyme preparation dissolved in a Tris-HCl buffer, pH 7.2 and containing 0.5M sodium chloride. In this case, a study of the chromatographic profile of the distribution of molecular masses of the N-acetylheparosan released enables it to be confirmed that the latter is an N-acetylheparosan consisting of longer chains, the maximum of the peak lying at approximately 9200 Da. This demonstrates that, in conjunction with an anion exchange resin, it is possible to vary the fragmentation of N-acetylheparosan using membrane preparations having a given NaCl concentration.

Other Examples of Use of the Enzyme for the Fragmentation of a High Molecular Mass N-Acetylheparosan The use of the enzyme which is the subject of the present invention in the fragmentation of a high molecular mass N-acetylheparosan has also been illustrated in Example 1, and in particular in:

2- In vivo demonstration of the enzyme in a fermenter.

3- Localisation of the enzyme - Production of preparations containing this enzyme.
  Step A - Production of a crude lysate possessing enzymatic activity. Assessment of its activity; b) demonstration of the fragmentation produced by a crude lysate, and
  Step B - Production of a membrane preparation possessing enzymatic activity - Assessment of its activity.

4- Solubilisation of the enzyme

The above represent processes for fragmentation of a high molecular mass N-acetylheparosan which are also applicable at an industrial or semi-industrial level.

We claim:

1. A method for the fragmentation of high molecular mass N-acetylheparosan comprising the treatment of said N-acetylheparosan with a preparation containing an enzyme being obtained from the *Escherichia coli* (K5) strain SEBR 3282, or from a spontaneous or induced mutant of said strain, wherein said enzyme has a molecular mass between 62,000 and 70,000 Da, assessed by exclusion chromatography, has an isoelectricpoint in the pH range between 4.7 and 5.4 pH units, is an eliminase, is of membrane origin, has a temperature of optimal functioning (maximal activity) in the region of 37 ° C., and has an inactivated temperature at approximately 60° celsius, has an optimal pH range for its optimal functioning between the values of pH 6 and 7, has an optimal range of concentration of monovalent or divalent ions for its optimal range of concentration of monovalent or divalent ions for its optimal functioning in the vicinity of 0.2M.

2. A method for obtaining a N-acetylheparosan having molecular masses grouped together, lying between 2000 and 10,000 Da assessed by exclusion chromatography, comprising the treatment of high molecular mass N-acetylheparosan with a preparation containing an enzyme in the presence of a solution of sodium chloride, said enzyme being obtained from the *Escherichia coli* (KS) strain SEBR 3282, or from a spontaneous or induced mutant of said strain, having a molecular mass between 62,000 and 70,000 Da, assessed by exclusion chromatography, having an isoelectric point in the pH range between 4.7 and 5.4 pH units, and being an eliminase.

3. A method for the preparation of N-acetylheparosans as claimed in claim 2, comprising the treatment of said high molecular mass N-acetylheparosan with a preparation containing an enzyme in the presence of a solution of sodium chloride having a molarity of 0.2 to 0.5M, said enzyme being obtained from the *Escherichia coli* (K5) strain SEBR 3282, or from a spontaneous or induced mutant of said strain, having a molecular mass between 62,000 and 70,000 Da, assessed by exclusion chromatography, having an isoelectric point in the pH range between 4.7 and 5.4 pH units, and being an eliminase.

4. A method as claimed in claim 2, comprising the steps of binding said high molecular mass heparosan to a column of ion exchange resin, passing a preparation of an enzyme through the column of ion exchange resin, said enzyme being obtained from the *Escherichia coli* (K5) strain SEBR 3282, or from a spontaneous or induced mutant of said strain, having an isoelectric point in the pH range between 4.7 and 5.4 pH units, and being an eliminase, and eluting with a 0.2 to 0.5M solution of sodium chloride.

5. A method as claimed in claim 1, wherein the enzymatic reaction is performed between pH 4.0 and pH 9.0.

6. A method as claimed in claim 4, wherein the resin is of the anion exchanger type.

7. A method as claimed in claim 1, wherein the enzyme is used in immobilized form.

8. A method as claimed in claim 1, wherein the reaction is performed between pH 6.5 and pH 7.4.

9. A method as claimed in claim 1, wherein the enzyme is an endo-β-eliminase.

10. A method as claimed in claim 2, wherein the enzyme is an endo-β-eliminase.

11. A method as claimed in claim 3, wherein the enzyme is an endo-β-eliminase.

12. A method as claimed in claim 4, wherein the enzyme is an endo-β-eliminase.

* * * * *